United States Patent [19]

Eickholt

[11] 4,447,640

[45] May 8, 1984

[54] PREPARATION OF α-UNSATURATED CARBOXYLIC ESTERS AND AMIDES FROM 1,2-DIHALOALKANES BY CARBONYLATION

[75] Inventor: Kathryn A. Eickholt, Midland, Mich.

[73] Assignee: The Dow Chemical Company, Midland, Mich.

[21] Appl. No.: 378,672

[22] Filed: May 17, 1982

[51] Int. Cl.$^3$ .................... C07C 67/36; C07C 102/00
[52] U.S. Cl. .................... 560/207; 260/410; 260/410.5; 260/410.9 R; 564/132; 560/104
[58] Field of Search ............. 560/207, 213, 104; 570/207, 227; 564/132; 260/410, 410.5, 410.9 R

[56] References Cited

U.S. PATENT DOCUMENTS

| | | | |
|---|---|---|---|
| 2,210,563 | 8/1940 | Andrussow | 570/227 |
| 2,765,350 | 10/1956 | Conrad | 570/227 |
| 3,457,299 | 7/1969 | Closson et al. | 560/207 |
| 3,626,005 | 12/1971 | Scheben et al. | 260/544 A |
| 3,927,131 | 12/1975 | Ward | 570/227 |
| 3,988,358 | 10/1976 | Heck | 260/410.6 |

FOREIGN PATENT DOCUMENTS

1091042 11/1967 United Kingdom .

OTHER PUBLICATIONS

Scheben, John A. et al., Catal. Org. Syn., (Conf. 5th), pp. 181–201, (1975).
Kirk–Othmer *Encyclopedia of Chemical Technology*, 2nd Ed., vol. 13, (1967), 333, 348 and 349.
Heck, R. F. *Advances in Catalysis*, vol. 26, (1977), pp. 323–347.
Mitsubishi Rayon Co. *Chemical Abstracts*, vol. 71, (1969), No. 49317p, (French Pat. 1,541,977).
Yamagishi, Akio et al. *Chemical Abstracts* 75, (1971), No. 21744j.
Sato, Ryozi et al. *Chemical Abstracts* 76, (1972), No. 3403p.
Kawamura, Yuichi et al. *Chemical Abstracts* 76, (1972), No. 60282.
Sugita, Shigeski et al. *Chemical Abstracts*, vol. 83, (1975), No. 192582g.
Shimizu, Noboru et al. *Chemical Abstracts*, vol. 84, (1978), No. 18032f.
Sudo, Makoto et al., *Chemical Abstracts*, vol. 84, (1976), No. 90761k.
Ohtani, Mitsuo et al. *Chemical Abstracts*, vol. 88, (1978), No. 51330g.
Firsov et al. *Chemical Abstracts*, vol. 90, (1979), No. 169288u.

*Primary Examiner*—Natalie Trousof
*Assistant Examiner*—L. Hendriksen
*Attorney, Agent, or Firm*—Douglas N. DeLine; Norman L. Sims

[57] ABSTRACT

The invention is a process for preparing α-unsaturated carboxylic esters or amides comprising contacting a 1,2-dihaloalkane, an alcohol or amine, and carbon monoxide, in the presence of a catalytic amount of a group VIII metal at elevated temperatures and pressures. The invention further includes preventing the α-unsaturated carboxylic esters or amides prepared by the addition of a free radical inhibitor capable of improving catalyst lifetime to the reaction mixture.

21 Claims, No Drawings

PREPARATION OF α-UNSATURATED CARBOXYLIC ESTERS AND AMIDES FROM 1,2-DIHALOALKANES BY CARBONYLATION

BACKGROUND OF THE INVENTION

The invention is a process for the preparation of α-unsaturated carboxylic esters and amides. More specifically, the process is the carbonylation of a 1,2-dihaloalkane in the presence of an alcohol or amide to prepare an α-unsaturated carboxylic ester or amide.

α-Unsaturated carboxylic esters and amides have been prepared by the carbonylation of olefinic halides. See Heck, U.S. Pat. No. 3,988,358 (incorporated herein by reference), Scheben et al., U.S. Pat. No. 3,626,005 (incorporated herein by reference), and Closson, U.S. Pat. No. 3,457,299 (incorporated herein by reference).

Methyl halides represented by the formula $CX_nH_{4-n}$ wherein X is a halogen and n is an integer from 2 to 4 have been successfully carbonylated. See Mador et al., U.S. Pat. No. 3,454,632 (incorporated herein by reference).

Heck, Advances in Catalysis, 26, 323 at 327 (1977), teaches that saturated aliphatic halides cannot be carbonylated in the presence of palladium or nickel catalysts.

Surprisingly, saturated 1,2-dihaloalkanes have been found to undergo carbonylation under certain reaction conditions producing an α-unsaturated carboxylic ester or amide.

SUMMARY OF THE INVENTION

The invention is a process for preparing carboxylic esters or amides represented by the formula

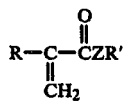
(I)

wherein:
R is hydrogen, alky or aryl;
R' is hydrogen, alkyl, cycloalkyl or benzyl and may be substituted with amines, hydroxyl groups or carboxylic acid groups; and
Z is O or NR';
comprising contacting a 1,2-dihaloalkane represented by the formula

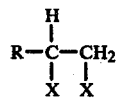
(II)

wherein R is as defined above and X is separately in each occurrence chlorine, bromine or iodine; with an alcohol or amine represented by the formula

 (III)

wherein R' and Z are as defined above; and carbon monoxide in the presence of a catalytic amount of a group VIII metal at elevated temperature and pressure.

The invention further includes the use of a free radical inhibitor to maintain catalyst life during the preparation of the α-unsaturated carboxylic esters or amides.

DETAILED DESCRIPTION OF THE INVENTION

The process for preparing α-unsaturated carboxylic esters and amides by contacting a 1,2-dihaloalkane with carbon monoxide and an alcohol or amine in the presence of a catalytic amount of a group VIII metal at elevated temperatures and pressures can be represented by the following equations, equation IV where R'ZH is an alcohol, R'OH, and equation V where R'ZH is an amine, $R_2'NH$:

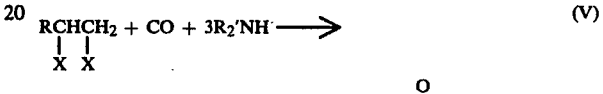

wherein R, R' and X are defined above.

The 1,2-dihaloalkane can have an R which is hydrogen, alkyl or aryl. R is preferably $C_{1-10}$ alkyl, most preferably methyl. X is preferably chlorine. In one embodiment of this invention, the 1,2-dihaloalkane is 1,2-dichloropropane.

To prepare an α-unsaturated carboxylic ester, R'ZH must be an alcohol, and can be primary, secondary or tertiary. Primary alcohols are more reactive than secondary alcohols, which are more reactive than tertiary alcohols. In this embodiment, R' is preferably $C_{1-12}$ alkyl or benzyl. More preferably the starting alcohols include methanol, ethanol, lauryl alcohol or benzyl alcohol, and is most preferably methanol.

To prepare an amide, R'ZH must be a primary or secondary amine or ammonia.

The best yields of α-unsaturated carboxylic esters or amides are achieved when the molar ratio of alcohol or amine to 1,2-dihaloalkane is 3:1 or greater. In this process, one mole of alcohol or amine adds to the carbonyl group on the 2 carbon on the 1,2-dihaloalkane. The second and third mole of alcohol or amine react with the halogen or the hydrogen halides leaving the dihaloalkane to prevent the presence of large amounts of free hydrogen halides or halogens in the reaction vessel during the reaction. As a result, side products of this process are alkyl or aryl halides when alcohols are starting reagents, and amine salts where amines are starting reagents.

Carbon monoxide is usually introduced in large excesses. This is achieved by maintaining positive pressure of carbon monoxide in the reaction vessel. Usually the elevated reaction pressure is maintained with carbon monoxide gas. It is desirable to use between 1.5 and 25 moles or more of carbon monoxide per mole of 1,2-dihaloalkane to be carbonylated. A preferred excess is from about 2 to about 15 moles, and a most preferred ratio is from about 3 to about 12 moles of carbon monoxide per each mole of 1,2-dihaloalkane.

This process may be run in either the vapor or the liquid phase. Where X is chlorine, the vapor phase is preferred. Where X is bromine, the liquid phase is preferred. Where R'ZH is an amine the liquid phase is preferred.

The catalysts are various forms of group VIII metals including palladium, nickel, platinum, iridium, and rhodium. Mixtures of the group VIII metals can also be used. The catalyst is preferably palladium or nickel, and most preferably palladium. These catalysts may be employed in both the heterogeneous and homogeneous forms.

In heterogeneous form, the metal can be on a support which can be any inert matrix. Suitable supports include alumina, carbon, silica, charcoal, diatomaceous earth, bentonite, firebrick, kaolin, ground glass, silicon carbide, silica gel and the like. Preferred supports include alumina and carbon, most preferred is alumina.

When the catalyst is supported palladium, between 0.1 and 5 percent palladium by weight of the support will catalyze this reaction, and between 0.1 and 1.0 percent is preferable.

Colloidal dispersions of these catalysts in an inert liquid reaction medium can also be used.

Complexes of group VIII metals can be used as homogeneous catalysts by adding salts of such metals to the reaction mixture. These catalysts usually must be used in conjunction with a triorganic phosphine or phosphite, in which case, triorganophosphine or triorganophosphite complexes are formed under the reaction conditions. In order for the complexes to be catalytic, the group VIII metal in the complex must be reducible to the zero valence state. Catalyst concentrations of from about 0.01 mole percent to about 10.0 mole percent or more may be used, preferably about 0.1 to 2 percent.

The process can be carried out in inert reaction media. For example, it can be carried out in the presence of a liquid reaction medium and/or dispersing medium which does not enter into the reaction. The liquid reaction medium is an inert organic liquid such as hydrocarbon or mixtures thereof. Hydrocarbons which can be employed can be either aliphatic, alicyclic or aromatic. Typical applicable liquid reaction media are cyclohexane, benzene, toluene, isooctane, xylene, mesitylene, ether, kerosene, No. 9 oil and the like.

The process can be carried out in reactive liquid reaction media, that is, in a reaction medium which enters into the reaction with the carbonyl group. The liquid reaction media may be alcohols or amines which would yield respectively esters or amides.

The carbonylation of vinylic halides to prepare $\alpha$-unsaturated esters or amides has been disclosed by Heck, U.S. Pat. No. 3,988,358; Scheben et al., U.S. Pat. No. 3,626,005; and Closson, U.S. Pat. No. 3,457,299. It has been discovered that mixtures of 1,2-dihaloalkanes and vinyl halides may be carbonylated to $\alpha$-unsaturated esters and amides by the process disclosed herein. These vinyl halides are represented by the formula $R_2C=C(X)R$, wherein R is as defined above. In one embodiment of this invention, a mixture of 1,2-dichloropropane and 2-chloropropene can be carbonylated in the presence of methanol to prepare methyl methacrylate.

Elevated temperatures are used in this carbonylation process. Suitable temperatures are between about 100° C. and 400° C., most preferably 150° C. to 300° C.

Those 1,2-dihaloalkanes wherein X is bromine, carbonylate at lower temperatures than where X is chlorine because bromine is more reactive.

This process is performed with elevated pressure. Usually carbon monoxide gas is used to pressurize the reaction vessel or zone. The pressure can be between about 100 and 5000 psi, preferably between about 400 and 1000 psi, and most preferably between about 400 and 800 psi.

Polymerization can take place during the preparation of these compounds. Where a mixture of 1,2-dichloroalkane and vinylic halides are used, the unsaturated vinylic halides can polymerize. Further, it is believed that the 1,2-dihaloalkanes and vinylic halides may decompose and deposit carbon on a heterogeneous catalyst support, thereby fouling the catalyst and reaction zone. Such polymerization can foul up the reaction vessel or zone, or the catalyst where a heterogeneous catalyst is used. It has been discovered that the addition of an amount of free radical inhibitor during the carbonylation process described above prevents polymerization and fouling of the reaction vessel or zone and any heterogeneous catalyst by the deposit of carbon thereon. It has been further discovered that the use of these free radical inhibitors during the reaction increases the active life of the catalyst dramatically. Suitable free radical inhibitors include phenols, cresols, xylenols, naphthols, catechols, trihydroxybenzenes, quinones, phenothiazines, phenoxazines and phenazines. Preferred free radical inhibitors include phenol, 2,6-di-tert-butyl-p-cresol, and p-methoxyphenol.

Suitable amounts of the free radical inhibitor are between 0.001 and 10 percent by weight of the reaction mixture.

The use of these free radical inhibitors improves the product yield and the catalyst life, especially where the catalyst is heterogeneous.

The free radical inhibitors can be used to prevent polymerization where either a 1,2-dihaloalkane, a vinyl halide or a mixture of both are being carbonylated.

SPECIFIC EMBODIMENTS

The invention disclosed herein having been fully described, the following examples are included solely to illustrate the invention and are not intended to limit the scope of the invention.

EXAMPLE 1

One mole of 1,2-dichloropropane, 2.6 moles of methanol, 0.1 gram of 2,6-di-tert-butyl-p-cresol and 12.6 grams of benzene (used as internal standard for gas chromatograph analysis) were mixed and fed in the vapor phase at a rate of 4 g/hr over a 0.3 percent palladium on alumina catalyst in the presence of carbon monoxide. The temperature was 240° C., the pressure 400 psi, and the carbon monoxide flow was 50 cc/min. A sample taken 1 hour and 45 minutes after the start of the reaction showed a 66 percent conversion of 1,2-dichloropropane and 21 percent selectivity to methyl methacrylate. Methyl chloride was coproduced.

EXAMPLE 2

A mixture of 0.02 gram of 2,6-di-tert-butyl-p-cresol, 64.5 grams of methanol, 10.6 grams of benzene (internal standard for gas chromatographic analysis) and 129.3 grams of 2-chloropropene were fed at a rate of 4 g/hr over 20 ml of 0.3 percent palladium on alumina catalyst. At the same time, carbon monoxide was fed over the catalyst at over 50 cc/min. The temperature was 220° C. and the pressure was 400 psi. Analysis of the product stream after 3 hours shows a 28.5 percent yield of methyl methacrylate. The catalyst deactivation rate was 0.6 percent per hour.

EXAMPLE 3

The same reaction as in Example 2 without the 2,6-di-tert-butyl-p-cresol was run. The yield of methyl methacrylate was 19 percent. Catalyst deactivation rate was 1.2 percent per hour.

Examples 2 and 3 demonstrate the effect of the use of free radical inhibitors in the processes disclosed herein. The yield of product was increased when the free radical inhibitors were used. These examples further demonstrate that the free radical inhibitors reduce the catalyst deactivation rate by a factor of two.

What is claimed is:

1. A process for preparing α-unsaturated carboxylic esters or amides represented by the formula

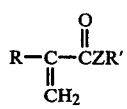

wherein:
R is hydrogen, alkyl or aryl;
R' is hydrogen, alkyl, cycloalkyl or benzyl which may be substituted with amine groups, hydroxyl groups or carboxylic acid groups; and
Z is O or NR';
comprising contacting a 1,2-dihaloalkane represented by the formula

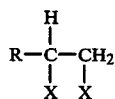

wherein R is as defined above and X is separately in each occurrence chlorine, bromine or iodine; with an alcohol or amine represented by the formula
R'ZH
wherein R' and Z are as defined above; and with carbon monoxide in the presence of a catalytic amount of a group VIII metal at elevated temperature and pressure.

2. The process of claim 1 which further includes the presence of a free radical inhibitor adapted for increasing the catalyst lifetime during this process.

3. The process of claim 2 wherein the free radical inhibitor is a phenol, cresol, xylenol, naphthol, catechol, trihydroxybenzene or quinone.

4. The process of claim 3 wherein the free radical inhibitor is phenol, 2,6-di-tert-butyl-p-cresol, or p-methoxyphenol.

5. The process of claim 2 wherein the catalyst is nickel or palladium on a support.

6. The process of claim 5 wherein the catalyst is palladium on alumina, silica or carbon.

7. The process of claim 5 wherein the reaction is run in the vapor phase.

8. The process of claim 7 wherein the temperature is between about 150° C. and 300° C.

9. The process of claim 7 wherein the pressure is between about 100 and 5000 psi.

10. The process of claim 9 wherein the pressure is between about 400 and 1000 psi.

11. The process of claim 2 wherein X is chlorine.

12. The process of claim 2 wherein R is $C_{1-10}$ alkyl.

13. The process of claim 12 wherein R is methyl.

14. The process of claim 2 wherein the 1,2-dihaloalkane is 1,2-dichloropropane.

15. The process of claim 2 wherein the R'ZH is methanol, ethanol, lauryl alcohol or benzyl alcohol.

16. The process of claim 15 wherein R'ZH is methanol.

17. The process of claim 2 wherein the catalyst is a palladium complex reducible to palladium in the zero valence state under the reaction condition.

18. The process of claim 17 in which the palladium complex is either added as a catalyst or such a complex is formed under the reaction conditions by adding a triorganophosphorus compound and palladium metal or a palladium salt.

19. The process of claim 5 or 17 wherein the reaction is run in the liquid phase.

20. The process of claim 2 wherein the α-unsaturated esters or amides are prepared from a mixture of 1,2-dihaloalkane and a vinyl halide.

21. The process of claim 20 wherein the 1,2-dihaloalkane is 1,2-dichloropropane and the vinyl halide is 2-chloropropene.

* * * * *